US010808275B2

(12) United States Patent
Cellier et al.

(10) Patent No.: US 10,808,275 B2
(45) Date of Patent: *Oct. 20, 2020

(54) USE OF AT LEAST ONE CHROMOGENIC AND/OR FLUOROGENIC PHOSPHATASE SUBSTRATE FOR THE DETECTION AND/OR ENUMERATION OF ENTEROBACTERIA IN A SAMPLE

(71) Applicant: BIOMERIEUX, Marcy-l'Etoile (FR)

(72) Inventors: Marie Cellier, Montalieu-Vercieu (FR); Marie-Pierre Bourguignon, Perouges (FR); Diane Halimi, Saint Maurice de Beynost (FR); Sylvain Orenga, Neuville-sur-Ain (FR)

(73) Assignee: BIOMÉRIEUX, Marcy-l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/782,122

(22) PCT Filed: Apr. 1, 2014

(86) PCT No.: PCT/EP2014/056544
§ 371 (c)(1),
(2) Date: Oct. 2, 2015

(87) PCT Pub. No.: WO2014/161864
PCT Pub. Date: Oct. 9, 2014

(65) Prior Publication Data
US 2016/0046976 A1    Feb. 18, 2016

(30) Foreign Application Priority Data

Apr. 3, 2013 (FR) ..................... 13 53017

(51) Int. Cl.
*C12Q 1/10* (2006.01)
*C12Q 1/42* (2006.01)

(52) U.S. Cl.
CPC ............. *C12Q 1/42* (2013.01); *C12Q 1/10* (2013.01); *C12Y 301/03* (2013.01); *C12Y 302/01031* (2013.01); *Y02A 50/451* (2018.01)

(58) Field of Classification Search
None
See application file for complete search history.

(56) References Cited

U.S. PATENT DOCUMENTS

| | | |
|---|---|---|
| 4,892,817 A | 1/1990 | Pawlak |
| 5,210,022 A | 5/1993 | Roth et al. |
| 2005/0014215 A1 | 1/2005 | Gilbert et al. |
| 2005/0148044 A1* | 7/2005 | Rambach ............. C12Q 1/045 435/34 |
| 2008/0145879 A1* | 6/2008 | Orenga ............. C12Q 1/04 435/14 |
| 2008/0160555 A1* | 7/2008 | Rambach ............. C12Q 1/04 435/19 |
| 2010/0062467 A1 | 3/2010 | Monget et al. |

FOREIGN PATENT DOCUMENTS

| | | |
|---|---|---|
| EP | 1790734 A1 | 5/2007 |
| EP | 2107119 A1 | 10/2009 |
| FR | 2697028 A1 | 4/1994 |
| FR | 2790765 A1 | 9/2000 |
| WO | 2002/040706 A2 | 5/2002 |
| WO | 2004/027086 A1 | 4/2004 |
| WO | 2009/026920 A1 | 3/2009 |
| WO | WO 2010/0128120 A1 | 11/2010 |
| WO | 2011/080305 A1 | 7/2011 |
| WO | WO 2011/1077003 A1 | 9/2011 |
| WO | WO2012/161992 A1 | 11/2012 |
| WO | WO 2014/043616 A1 | 3/2014 |
| WO | WO 2014/12503 A1 | 7/2014 |

OTHER PUBLICATIONS

Pompei ("Patterns of Phosphatase Activity among Enterobacterial Species" International Journal of Systematic Bacteriology, 1993, 174-178). (Year: 1993).*
International Search Report dated Jun. 27, 2014 in corresponding International Patent Application No. PCT/EP2014/056544.
Satta et al., Phosphatase Activity Is a Constant Feature of All Isolates of All Major Species of the Family Enterobacteriaceae, Journal of Clinical Microbiology, Dec. 1988, pp. 2637-2641.
Looney et al., "Evaluation of the ATB 32 A System for Identification of Anaerobic Bacteria Isolated from Clinical Specimens," *J. Clin. Microbiol.* (Jul. 1990), 28(7):1519-1524.
Orenga et al., "Enzymatic Substrates in Microbiology," *J. Microbiol. Meth.* (2009), 79:139-155.
Rice et al., "Assay for β-Glucuronidase in Species of the Genus *Escherichia* and Its Applications for Drinking-Water Analysis," *Applied Environ. Microbiol.* (Feb. 1991), 57(2):592-593.
Von Graevenitz et al., "RADIPEC UR, a 2-h Miniaturized System for Pinpointing Uropathogens," *J. Clin. Microbiol.* (Jan. 1998), 26(1):151-152.
Third examination report for EP14714282.2 dated Aug. 29, 2018.
Agban et al., "Synthesis of Indigogenic Substrates. Investigation of *Salmonella* Esterase Activity," Eur. J. Med Chem. (1990), 25:697-699.
Baumstummler et al., "Development of a Nondestructive Fluoescence-Based Enzymatic Staining of Microcolonies for Enumerating Bacterial Contamination in Filterable Products," J. Applied Microbiol. (2010), 110:69-79.
Dickinson et al., "Stability of Emulsions Containing Both Sodium Caseinate and Tween 20," J. Colloid Interface Sci. (1999), 212:466-473.
International Search Report for PCT/FR2013/053259 dated Apr. 15, 2014.
"WO 2011/107703 A1" English machine translation, 2001, 48 pages of PDF.
Barber, et al., "Identification of *Staphylococcus pyogenes* by the Phosphatase Reaction", Journal of Pathology and Bacteriology, vol. 63, No. 1, Jan. 1, 1951, pp. 65-68.
Bobey et al., "Rapid Detection of Yeast Enzymes by Using 4-Methylumbelliferyl Substrates", Journal of Clinical Microbiology, vol. 13, No. 2, Feb. 1, 1981, pp. 393-394.
First Examination Report for EP14714282.2 dated Oct. 17, 2017.

* cited by examiner

*Primary Examiner* — Robert J Yamasaki
*Assistant Examiner* — Charles Z Constantine
(74) *Attorney, Agent, or Firm* — Husch Blackwell LLP

(57) ABSTRACT

Use of at least one chromogenic and/or fluorogenic phosphatase substrate for the detection and/or enumeration of enterobacteria in a sample likely to contain them, such as a food sample.

22 Claims, No Drawings

USE OF AT LEAST ONE CHROMOGENIC AND/OR FLUOROGENIC PHOSPHATASE SUBSTRATE FOR THE DETECTION AND/OR ENUMERATION OF ENTEROBACTERIA IN A SAMPLE

CLAIM OF PRIORITY

This application is a U.S. national stage filing under 35 U.S.C. § 371 of International Application No. PCT/EP2014/056544 filed on Apr. 1, 2014 entitled "USE OF AT LEAST ONE CHROMOGENIC AND/OR FLUOROGENIC PHOSPHATASE SUBSTRATE FOR THE DETECTION AND/OR ENUMERATION OF ENTEROBACTERIA IN A SAMPLE," which claims priority from French Application No. 1353017 filed Apr. 3, 2013, both of which are incorporated herein by reference in their entirety.

TECHNICAL FIELD

The present invention relates to the field of microbiology, and more particularly industrial microbiology. More specifically, the present invention relates to the detection and/or enumeration of enterobacteria (Eb) in a sample likely to contain (or suspected of containing) them, such as a food sample (human and animal food products), or in a production environment sample.

STATE OF THE ART

In order to safeguard consumer health, products marketed by the agri-food industry (meat products, dairy products, marine products, plant products, etc.) are subjected to numerous microbiological tests in order to ensure their safety (non-toxicity). Numerous solutions are currently employed to this end, including:

The detection and/or enumeration of pathogenic germs by using culture media, tasks which can be automated, for example using a VIDAS®, BacT/ALERT® or Tempo® apparatus, The enumeration of said pathogenic germs, in particular by using ad hoc culture media, The identification of micro-organisms, for example by using specific culture media, or API®/ID 32 systems, or in an automated manner with the VITEK® range, etc.

Analyses are largely performed in accredited laboratories, which are obliged to use methods recognised as compliant with international standards such as the ISO standards.

One of the primary ISO standards relating to food quality control is standard ISO 21528-2, entitled "Microbiology of food and animal feeding stuffs—Horizontal methods for the detection and enumeration of Enterobacteriaceae". As its title indicates, the above-mentioned standard is concerned with the detection and/or enumeration of enterobacteria. The latter are generally normal or pathological hosts, depending on the microbial species, of the human and animal digestive tracts. They seem more specifically adapted to humans or animals; some are responsible for sometimes severe human infections (typhoid fever, bacillary dysentery, plague). Enterobacteria are well known to the person skilled in the art, and have been characterized in the literature in particular by their bacteriological characteristics (morphology, behavior in cultures, biochemistry, antigenic structure, etc.). In general, the definition of enterobacteria can be considered as being based on the following criteria:

Gram-negative (Gram-) bacilli,
immobile or mobile on peritrichous cilia,
facultatively aerobic—anaerobic, breaking down glucose by fermentation (fermenting glucose), oxidase-negative and nitrate-reducing,
unsporulated.

Many intestinal enterobacteria can, to various degrees, be damaging to humans. They are known as "opportunistic pathogens". The frequency of their pathological manifestations is increasing, since it is often due to the existence, in these species, of antibiotic resistance plasmids allowing their selection and promoting dismicrobisms to their advantage. This character is particularly well-established with the species *Klebsiella pneumoniae*, a host of the airways which can be responsible for infections.

Other enterobacteria are known as "specific pathogens", and are particularly likely to cause digestive infections (diarrhea, gastroenteritis, enteritis, dysentery, mesenteric adenitis, septicemic fevers, etc.).

By way of example of "specific pathogens", non-exhaustive mention may be made of bacteria belonging to the genera *Salmonella, Shigella, Yersinia* and *Escherichia coli*.

A known culture medium, namely the chromID® *Coli* medium (previously marketed under the name "*Coli* ID"; ref. 42 017), aims to detect and enumerate coliform bacteria and beta-glucuronidase-positive *Escherichia coli* (Ec) (β-GUR +; also known as "GUR" [Rice et al. (1991), von Gravenitz et al. (1992)], "beta-Gur" [Looney et al. (1990)] or even "β-GUS" in the literature) in human and animal food products, as well as in production environment samples. It is an agar culture medium in a bottle. For all useful purposes, it should be noted that beta-glucuronidase enzymatic activity is listed under the title EC 3.2.1.31 in the international classification.

The term coliform is a generic term encompassing different bacteria families and having, amongst others, the characteristics of being Gram-, oxidase-, and fermenting lactose with production of acid and gas at a temperature of 30 or 37° C. in the presence of bile salts (see standard ISO 4831 from 1991). Coliforms are part of the Enterobacteria family, but not all enterobacteria have the above-mentioned characteristics. Species such as *E. coli* or certain species of the genera *Klebsiella, Enterobacter, Citrobacter* are coliforms. They are referred to as thermotolerant if they possess the same properties at a growth temperature of 44° C. Non-enterobacteria which possess these properties (e.g. *Aeromonas*) may also be considered as coliforms.

However, non-coliform enterobacteria (such as bacteria of the genus *Salmonella*) have a considerable pathogenic capacity, and as such, must also be the subject of microbiological controls aimed at detecting and/or enumerating them. That is why the aforementioned standard ISO 21528-2 does not stipulate detecting/enumerating only coliforms, but also enterobacteria in general.

So there is a need to develop an efficient, robust technique which is easy to implement, allowing the detection and/or enumeration of the enterobacteria present in a given sample, originating for example from a food batch. Preferably this technique must be sufficiently sensitive while satisfying the requisite specificity criterion, namely preventing, as far as possible, detection and/or enumeration of "false positives", namely for example the detection and/or enumeration of non-fermenting Gram-negative bacteria.

A chromogenic culture medium marketed by AES Chemunex, the REBECCA® medium, is regarded as making it possible to enumerate beta-glucuronidase-positive (β-GUR+) *Escherichia coli* (Ec) and enterobacteria on the same Petri dish. The colonies formed by the enterobacteria (including any *E. coli* colonies) are coloured red, and β-GUR+*E. coli* colonies exhibit dual coloration, namely on the one hand said red coloration, and on the other a blue-green coloration due to cleavage of a substrate from the enzyme β-glucuronidase (β-GUR), 5-bromo-4-chloro-3-indoxyl-beta-D-glucuronic acid (denoted X-GUR, also called 5-bromo-4-chloro-3-indolyl-beta-D-glucuronic acid), by β-GUR+*E. coli* bacteria. To the observer, the β-GUR+*E. coli* colonies exhibit a purplish coloration in their centre, corresponding to the mixture of red and blue colours, and a blue coloration on the edges of said colonies. Although providing satisfactory results, this REBECCA® medium possibly leads to "false positives", and may result in a food batch being locked down and destroyed because of suspicion of the presence of enterobacteria. Indeed, above a predefined quantity or concentration of enterobacteria (threshold value), the food batches tested are locked down and then destroyed. So these batches will not be placed on the market, and consequently will represent a financial loss for the company marketing them. Positive results obtained on the REBECCA® medium (threshold value exceeded) may be due, besides the red coloration due to enterobacteria, to that attributable to non-fermenting Gram-negative bacteria, which are generally less pathogenic than the former. In other words, even if the quantity of enterobacteria grown on the REBECCA® medium is below the threshold value in absolute terms, the food batch will be deemed unfit for consumption due to the non-fermenting Gram-negative bacteria colonies detected, just like the enterobacteria, through a red coloration on the REBECCA® medium. Even if the detection specificity of the REBECCA® medium is satisfactory overall, there nevertheless exists a need to improve this detection specificity.

Standards relating to media for the detection and/or enumeration (counting) of *Escherichia coli* based on detection of beta-glucuronidase activity describe media for the detection and/or enumeration of enterobacteria based on acidification of glucose, associated with a confirmation test. Consequently, to design a medium simultaneously allowing the detection and/or enumeration of *E. coli* and enterobacteria, the person skilled in the art would naturally be inclined to combine detection and/or enumeration of beta-glucuronidase activity and acidification of glucose within the same culture medium. However, this approach is limited, since the necessary glucose concentrations are high, and would most probably inhibit the detection of the beta-glucuronidase activity sought. Of course, it is necessary that the growth of the enterobacteria likely to be present in the tested sample is not inhibited in full or in part because of the substrates and other reagents used in the bacterial culture medium.

STATEMENT OF THE INVENTION

The objective of the present invention therefore consists in resolving all or some of the problems mentioned above.

Consequently, one of the objects of the present invention relates to the use of at least one chromogenic and/or fluorogenic phosphatase substrate for the detection and/or enumeration of enterobacteria in a sample likely to contain them (or suspected of containing them), such as a food sample.

Indeed, the Applicant has discovered, contrary to all expectations, that the enterobacteria likely to be present in a sample, such as a food sample, shared a common phosphatase enzymatic activity. Although phosphatase activity has already been described in relation to certain specific enterobacteria species, taken individually, nothing in the prior art suggested that this phosphatase enzymatic activity was shared by all enterobacteria likely to be found in a sample, and in particular in a food sample.

"Sample" is understood to mean a small part or small quantity isolated from an entity for analysis. This may be a clinical sample, human or animal, from a sampling of biological liquid, or a food sample, from any type of food, or a food processing or production environment sample. Thus this sample may be liquid or solid. Non-exhaustive mention can be made of a clinical sample of whole blood, serum, plasma, urine, faeces, of specimens from the nose, throat, skin, wounds, cerebro-spinal fluid, a sample of food, water, beverages such as milk, a fruit juice, yogurt, meat, eggs, vegetables, mayonnaise, cheese, fish, a food sample from an animal feed, such as in particular a sample from animal meals, a sample for surface or water testing. This sample may be used as-is, or, prior to analysis, undergo preparation such as enrichment, dilution, extraction, concentration, purification, in accordance with the methods known to the person skilled in the art.

"Food sample" is understood to mean, for the purpose of the present invention, a sample from a given food batch, on which microbiological tests can be performed.

By extrapolation, this sample may also be referred to as a "biological sample" insofar as it is likely to contain/suspected of containing biological material (namely at least enterobacteria).

Detection of enterobacteria makes it possible to reveal, to the naked eye or using an optical apparatus, the existence of growth of the target bacteria (in this case enterobacteria), namely the appearance of coloured and/or fluorescent colonies (depending on whether a chromogenic or fluorogenic substrate is used, or one presenting both characteristics simultaneously), said colonies being coloured and/or fluorescent by revealing the phosphatase enzymatic activity of the enterobacteria on said phosphatase substrate. Generally, the detection works by means of an optical apparatus for fluorogenic substrates, or by the naked eye or using an optical apparatus for coloured substrates. Advantageously, detection can also enable identification of the target bacteria.

Enumeration of enterobacteria meanwhile consists in counting the number of enterobacteria colonies which have grown on this culture medium, employing microbiology techniques well known to the person skilled in the art.

Use of a chromogenic and/or fluorogenic phosphatase substrate makes it possible to obtain a very satisfactory detection sensitivity, while conferring very good specificity: most non-enterobacteria Gram-negative bacteria (for example non-fermenting Gram-negative) are not coloured and/or fluorescent.

Furthermore, such a phosphatase substrate has very little—or even no—inhibiting effect on enterobacteria growth on the culture medium, which represents a considerable advantage.

Chromogenic and/or fluorogenic substrate is understood to mean a substrate allowing the detection of enzymatic or metabolic activity of the target micro-organisms, by means of a directly or indirectly detectable signal. For direct detection, this substrate may be linked to a part acting as a fluorescent or coloured marker (Orenga et al., 2009; J. Microbiol. Methods; 79(2):139-55). For indirect detection, the reaction medium according to the invention may additionally contain a pH indicator, which is sensitive to pH variation caused by consumption of the substrate, and which reveals the metabolism of the target micro-organisms. Said pH indicator may be a chromophore or a fluorophore. As examples of chromophores, mention may be made of bromocresol purple, bromothymol blue, neutral red, aniline blue, and bromocresol blue. Fluorophores include for example 4-methylumbelliferone, hydroxycoumarin derivatives or resorufin derivatives.

"Chromogenic and/or fluorogenic phosphatase substrate" should be understood to mean an enzyme substrate capable, after reaction with a phosphatase enzyme, of generating a coloured and/or fluorescent product. The possible enzyme-substrate reactions are well known to the person skilled in the art. These may be cleavage reactions (for example by hydrolysis of the enzyme substrate), reduction, etc.

The chromogenic and/or fluorogenic phosphatase substrates used according to the present invention are preferably synthetic substrates, comprising two parts (preferably consisting of two parts), a first part specific to the enzymatic activity to be detected, namely a phosphatase enzymatic activity (i.e. a phosphate group), and a second part acting as a marker, hereafter referred to as the chromogenic and/or fluorogenic marker part. Said marker part is deemed "chromogenic and/or fluorogenic" insofar as when it is no longer associated with the first part, namely after cleavage by the phosphatase enzyme (for example in a hydrolysis reaction) and separation of said first and second parts, said marker part produces a coloration and/or a fluorescence. In other words, said chromogenic and/or fluorogenic marker part is able, under certain conditions, to give rise to a coloured and/or fluorescent reaction.

Fluorogenic substrates may have various compositions. Among these can be counted in particular those based on 7-hydroxycoumarin (umbelliferone) or 7-aminocoumarin and their derivatives substituted in positions 3, 4 (or 5 and 6), such as 4-methylumbelliferone for example, which enable the release of a fluorescent compound varying in colour from blue to green under an ultraviolet (UV) lamp.

Other fluorogenic substrates are based on resorufin (and derivatives thereof). They result in the release of a fluorescent pink compound under natural light ($\lambda ex=530$ nm).

Mention can also be made of substrates based on fluorescein (and derivatives thereof) which, after degradation, release a fluorescent yellow compound under natural light ($\lambda ex=485$ nm).

Because the fluorescence does not remain localized on the colonies, fluorogenic enzyme substrates based on the above-mentioned markers are generally unsuitable for use in agar media, and are more used in liquid media.

The chromogenic enzyme substrates usable within the terms of the present invention may be of various types.

Firstly, mention should be made of substrates based on indoxyl and derivatives thereof, which after hydrolysis and in the presence of oxygen, produce a precipitate varying from blue to pink. These substrates based on indoxyl and derivatives thereof are particularly preferred within the terms of the present invention due to their relative ease of use and their good sensitivity in the detection and/or enumeration of bacteria. Their applications primarily relate to osidase, esterase and phosphatase enzymatic activities (phosphatase being an esterase activity of phosphoric acid). Well suited to use on a solid or semi-solid support (filter, agar, electrophoresis gel, etc.), they are less well suited to use in a liquid medium (precipitate formation).

Certain Aldol®-based indoxyl derivatives represent enzyme substrates of interest within the terms of the present invention, insofar as the appearance of a coloured precipitate does not require any addition (oxygen, metal salts, etc.). Therefore use of such enzyme substrates may prove particularly advantageous as part of pour plate inoculation of the bacteria. These Aldol®-based indoxyl derivatives are particular indoxyl derivatives (1H-indolyl-3-yl), namely indoxyl-based substrates conjugated on cyclical amine (N-arylated), as disclosed in the PCT patent application published under reference WO 2010/128120 (in the name of Biosynth AG [CH]). These enzyme substrates can be obtained from Biosynth AG, and in particular can be ordered via the website of Biosynth AG, namely: http://www.biosynth.com.

Secondly, there are enzyme substrates based on hydroxyquinoline, dihydroxyanthraquinone, catechol, dihydroxyflavone or esculetin and their derivatives, which, in the presence of iron salts, produce a coloured precipitate. In this case too, their applications relate primarily to osidase, esterase and phosphatase enzymatic activities.

Thirdly, mention can be made of enzyme substrates based on nitrophenol and nitroaniline and derivatives, which result in the formation of a yellow compound. They make it possible to detect osidase, esterase and phosphatase activities in the case of nitrophenol-based substrates, and peptidase activities in the case of nitroaniline-based substrates. However, in the case of detection of peptidase activities, the nitroaniline released is toxic to the bacteria that are to be identified or characterized, which can prove detrimental to analyses in progress or subsequent analyses. On the other hand, they are generally unsuitable for use on a solid support, and better suited to use in a liquid medium. In addition, they are low-chromogenic due to the relatively low extinction coefficient of the colour (yellow), the contrast of which is weak in biological media (which influences the detection sensitivity of the corresponding microbiological tests).

Fourthly, there are enzyme substrates based on naphthol and naphthylamine and their derivatives. In this case, the enzyme-substrate reaction takes place in two stages, with the naphthol or naphthylamine released by the enzymatic activity undergoing "azo-coupling" in the presence of a diazonium salt, which is added upon revelation, leading to the formation of a coloured insoluble compound. They make it possible to detect osidase and esterase activities by means of naphthol, and peptidase activities by means of naphthylamine. The "azo-coupling" reaction takes place in an often chemically aggressive medium which is toxic to bacteria and which makes the sample unusable for other analyses, and in addition naphthylamines are carcinogenic.

The present invention consequently makes it possible to discriminate without excessive effort enterobacteria (coloured and/or fluorescent) from non-enterobacteria (non-coloured and/or non-fluorescent), such as non-fermenting Gram-negatives. The fact that most Gram-negative non-enterobacteria are not coloured when using a chromogenic and/or fluorogenic phosphatase substrate in a sample indicates a very good specificity of the phosphatase substrate. This represents a significant advantage over the various techniques and media developed in the prior art.

According to the present invention, the marker part of the chromogenic and/or fluorogenic phosphatase substrate is preferably chosen from substrates based on indoxyl (3-Indoxyl, 5-Bromo-3-indoxyl, 5-Iodo-3-indoxyl, 4-Chloro-3-indoxyl, 5-Bromo-4-chloro-3-indoxyl, 5-Bromo-6-chloro-3-indoxyl, 6-Bromo-3-indoxyl, 6-Chloro-3-indoxyl, 6-Fluoro-3 indoxyl, 5-Bromo-4-chloro-N-methyl-3-indoxyl, N-Methyl-3-indoxyl, Aldol® . . . ); on umbelliferone (4-Methylumbelliferone, Cyclohexenoesculetin, . . . ); on alizarin; on p-naphtholbenzein; on Nitrophenol (ortho-Nitrophenol, para-Nitrophenol, . . . ); on Hydroxyquinoline; on Catechol (Catechol, Dihydroxyflavone, Hydroxyflavone, . . . ); on Resorufin; on Chlorophenol Red; on Fluorescein; on Aminophenol (para-Aminophenol, Dichloro-aminophenol, . . . ); on Naphthol (alpha-Naphthol, 2-Naphthol, Naphthol-ASBI, . . . ); on Aminocoumarin (7-Amino-4-methyl-coumarin, . . . ); on Naphthylamide; on Acridine (Amino-phenyl-acridine . . . ); on Amino-phenoxazine (Amino-benzophenoxazinone, Amino-pentyl-resorufin, . . . ).

Preferably, the chromogenic and/or fluorogenic phosphatase substrate according to the present invention is selected from:

substrates based on indoxyl or a derivative thereof, such as 5-bromo-4-chloro-3-indoxyl-phosphate ("X-phosphate", abbreviated to X-P), 5-bromo-6-chloro-3-indoxyl-phosphate ("Magenta phosphate"), 6-chloro-3-indoxyl-phosphate ("Rose-phosphate", abbreviated to Rose-P), 5-iodo-3-indoxyl-phosphate, 6-bromo-3-indoxyl-phosphate, 5,6-dibromo-3-indoxyl-phosphate, 5-bromo-3-indoxyl-phosphate, Aldol® 458 phosphate, Aldol® 470 phosphate, Aldol® 484 phosphate, Aldol®495 phosphate, Aldol®515 phosphate, Aldol® n phosphate, and 3-hydroxyflavone-phosphate.

Regarding the nomenclature of enzyme substrates based on indoxyl or a derivative thereof, the roots "indoxyl" and "indolyl" should be understood as being equivalent. Thus X-phosphate may be called either "5-bromo-4-chloro-3-indoxyl-phosphate" or "5-bromo-4-chloro-3-indolyl-phosphate".

As indicated above, the phosphatase substrate is preferably a chromogenic substrate, advantageously cleavable by the phosphatase activity of the enterobacteria. Thus this chromogenic phosphatase substrate is, preferably, a substrate consisting of a target part and a marker part. Hydrolysis of the substrate by the phosphatase activity of the enterobacteria causes the separation (cleavage) of the target part and marker part, said target part characterizing the phosphatase enzymatic activity and said marker part being a molecule which makes it possible to reveal the hydrolysis reaction via the appearance of coloration on the hydrolysis site (colonies).

Advantageously, the phosphatase substrate is a substrate based on indoxyl or a derivative thereof. As an indoxyl-based phosphatase substrate, mention may be made in particular of 5-bromo-4-chloro-3-indoxyl-phosphate, 5-bromo-6-chloro-3-indoxyl-phosphate, 6-chloro-3-indoxyl-phosphate, 5-iodo-3-indoxyl-phosphate, 6-bromo-3-indoxyl-phosphate, 5,6-dibromo-3-indoxyl-phosphate, 5-bromo-3-indoxyl-phosphate, Aldol® 458 phosphate, Aldol® 470 phosphate, Aldol® 484 phosphate, Aldol®495 phosphate, Aldol®515 phosphate, Aldol® n phosphate. Preferably, 5-bromo-3-indoxyl phosphate ("Blue-Phosphate", abbreviated to Blue-P) is used.

According to a preferred embodiment, the phosphatase substrate is a substrate based on indoxyl or a derivative thereof, preferably chosen from 5-bromo-4-chloro-3-indoxyl-phosphate, 5-bromo-6-chloro-3-indoxyl-phosphate, 6-chloro-3-indoxyl-phosphate, 5-iodo-3-indoxyl-phosphate, 6-bromo-3-indoxyl-phosphate, 5,6-dibromo-3-indoxyl-phosphate, 5-bromo-3-indoxyl-phosphate, said phosphatase substrate being used in combination with an agent promoting oxidative polymerization of the indoxyl derivative, such as an ammonium ferric citrate metal complex. This polymerization reaction of the indoxyl derivative leads to the formation of an insoluble coloured compound.

The association of a phosphatase substrate based on indoxyl or a derivative thereof and an agent promoting oxidative polymerization of the indoxyl derivative, such as an ammonium ferric citrate metal complex, is generally recommended (or even necessary) for all phosphatase substrates based on indoxyl or a derivative thereof, with the exception of Aldol®-based indoxyl derivatives, as disclosed in the PCT patent application published under reference WO 2010/128120, for which colour and/or fluorescence generation is deemed "spontaneous", that is to say not requiring oxidation, nor the addition of said agent promoting oxidative polymerization of the indoxyl derivative, such as an ammonium ferric citrate metal complex. These Aldol®-based substrates, such as Aldol® 458 phosphate, Aldol® 470 phosphate, Aldol® 484 phosphate, Aldol®495 phosphate, Aldol®515 phosphate, Aldol® n phosphate, therefore represent particularly preferred phosphatase substrates within the terms of the present invention, especially under low dioxygen pressure conditions (for example in microaerophilia), which can go as far as anaerobiosis. As indicated above, they can be obtained from Biosynth AG, and in particular can be ordered via the website of Biosynth AG, namely: http://www.biosynth.com. The catalogue references (consultable in particular on the above-mentioned website) of the various Aldols® mentioned above are listed in table A, presented below:

TABLE A

| Name | BIOSYNTH ® catalogue reference |
|---|---|
| Aldol ® 470 phosphate, disodium salt | A-4678_P00 |
| Aldol ® 458 phosphate, disodium salt | A-4694_P00 |
| Aldol ® 495 phosphate, disodium salt | A-4704_P00 |
| Aldol ® 515 phosphate, disodium salt | A-4721_P00 |

By way of illustration, the Aldol® 470 phosphate, Aldol® 495 phosphate and Aldol® 515 phosphate substrates are defined by the general formula (I) represented below:

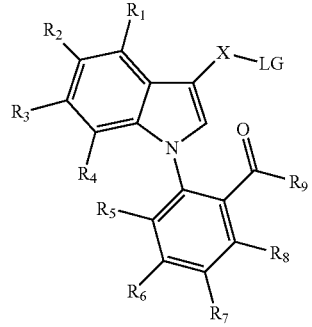

wherein groups R1, R2, R3, R4, R5, R6, R7, R8, R9, X and LG are as defined in table B below:

TABLE B

| Name | R1 | R2 | R3 | R4 | R5 | R6 | R7 | R8 | R9 | X | LG |
|---|---|---|---|---|---|---|---|---|---|---|---|
| Aldol ® 470 phosphate | H | H | H | H | H | H | H | H | H | R12 | phosphate |
| Aldol ® 495 phosphate | H | H | Cl | H | H | H | H | H | H | R13 | phosphate |
| Aldol ® 515 phosphate | H | H | H | H | H | H | H | H | H | R14 | phosphate | where

R12 = 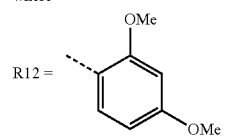

R13 = 

R14 = 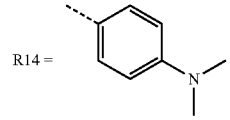

As "agent promoting oxidative polymerization of the indoxyl derivative of the phosphatase substrate", mention may be made of, in addition to ammonium ferric citrate and by way of examples, potassium permanganate and potassium ferricyanide.

The agent promoting oxidative polymerization of the indoxyl derivative (for example an ammonium ferric citrate metal complex) is used, preferably, at a concentration of between approximately 0.05 and approximately 0.9 mg/ml, preferably of around 0.3 mg/ml.

The agent promoting oxidative polymerization of the indoxyl derivative (preferably an oxidizing metal complex) makes it possible in particular to intensify the colours obtained within the colonies by catalyzing the oxidative polymerization of the indoxyl derivative, thus leading to the formation of an insoluble coloured compound.

The concentration at which the chromogenic and/or fluorogenic phosphatase substrate must be used in the culture medium containing the sample is easily determinable by the person skilled in the art based on their general knowledge, and if applicable, routine tests. This concentration must be sufficient to achieve the requisite detection sensitivity level, but must not be excessive, so as not to risk inhibiting the enterobacteria growth. By way of example, the concentration of this phosphatase substrate in the culture medium containing the sample to be tested is between approximately 0.05 and approximately 0.3 g/L, preferably between approximately 0.15 and 0.25 g/L, and advantageously of around 0.175 g/L.

According to a particularly preferred embodiment, the phosphatase substrate is contained in a composition comprising at least one, preferably two, and advantageously three of the following constituents:
  a bacterial culture medium suited to the bacteria to be detected (enterobacteria),
  an anti-Gram-positive selective system,
  an antifungal agent.

Advantageously, said composition comprises a bacterial culture medium suited to the bacteria to be detected (enterobacteria) and at least one of, and preferably both of, the following constituents:
  an anti-Gram-positive selective system,
  an antifungal agent.

According to a particularly preferred embodiment, this composition is a chromogenic and/or fluorogenic reaction medium. The latter allows the detection and/or enumeration of enterobacteria in a sample likely to contain (or suspected of containing) enterobacteria.

"Reaction medium" is understood to mean a medium comprising all the elements necessary for the expression of metabolism and/or for the growth of micro-organisms. The reaction medium may be solid, semi-solid or liquid. Solid medium is understood to mean for example a gelled medium. Agar is the traditional gelling agent in microbiology for culturing micro-organisms, but it is possible to use gelatin, agarose or other natural or artificial gelling agents. There are a number of commercially available preparations, such as for example Columbia agar, Trypticase-soy agar, MacConkey agar, Mueller Hinton agar or more generally those described in the Handbook of Microbiological Media (CRC Press). Said reaction medium may comprise one or more elements in combination, such as amino acids, peptones, carbohydrates, nucleotides, minerals, vitamins, etc. The medium may also comprise a colorant. As a guide, Evans blue, neutral red, sheep blood, horse blood, an opacifier such as titanium oxide, nitroaniline, malachite green, brilliant green, one or more metabolic indicators, one or more metabolic regulators, etc. may be mentioned as colorants.

Within the terms of the present invention, the reaction medium consists of both a culture medium and a revealing medium.

Regarding the bacterial culture medium suited to the bacteria to be detected, this shall be chosen without difficulty by the person skilled in the art as a culture medium promoting enterobacteria growth.

According to a preferred embodiment, pour plate inoculation is performed, namely 1 mL of the sample to be tested is dispersed in the bottom of a Petri dish, and then the culture medium (for example agar medium) is poured on top. The enterobacteria then develop within the mass of the agar medium and give rise to colonies. As part of this pour plate inoculation, the enterobacteria are cultured under microaerophilic conditions.

Use of at least one anti-Gram-positive (anti-Gram+) selective system and/or at least one antifungal agent (preferably both) is recommended within the terms of the present invention, since it makes it possible for the selectivity to be improved.

The anti-Gram-positive (anti-Gram+) selective systems and/or antifungal systems are well known to the person skilled in the art. By way of example, in the anti-Gram-positive selective system used for the purpose of the present invention, one or more selective agent(s) are used, selected from the group consisting of: bile salts (by way of example sodium deoxycholate, sodium glycocholate, or a mixture of several bile salts), crystal violet, Tergitol® 4 or Niaproof® 4. Preferably, deoxycholate and crystal violet are used at concentrations known to the person skilled in the art in order to achieve the desired effect, namely eliminating the Gram-positive bacteria.

"Selective agent" is understood to mean any compound capable of preventing or slowing the growth of a micro-organism other than the target micro-organism. Without being restrictive, a concentration of between 0.01 mg/l and 5 g/l in selective agent(s) is particularly suited to the present invention.

Antifungal ("or antifungal agent") is understood to mean any compound able to prevent or slow the growth of a yeast or a mould. As a guide, mention may be made in particular of amphotericin B, fluconazole, itraconazole, voriconazole and cycloheximide. Preferably, at least one antifungal agent is used at concentrations known to the person skilled in the art to obtain the above-mentioned effect.

"Antibiotic" is understood to mean any compound able to prevent or slow the growth of a bacterium. Antibiotics belong in particular to the beta-lactams, glycopeptides, aminosides, polypeptides, sulfamides, and quinolones groups. As a guide, mention may be made in particular of the antibiotics cefotaxime, cefsulodin, ceftazidime, cefoxitin, ceftriaxone, cefpodoxime, aztreonam, vancomycin, gentamicin, Trimethoprim, tobramycin, moxalactam, fosfomycin, D-cycloserine, Polymixine, Colistine, and quinolones such as nalidixic acid.

The enterobacteria likely to be present in a sample—and more particularly in a sample of food origin—are known to the person skilled in the art. By way of example, mention may be made of the enterobacteria in the group consisting of: *E. coli, Salmonella, Klebsiella, Citrobacter, Yersinia* etc. As stated above, it was discovered by the Applicant, against all expectations, that these enterobacteria shared a common phosphatase activity.

The composition according to the invention (chromogenic and/or fluorogenic medium according to a preferred embodiment) may, of course, comprise other constituents in order to optimize the detection and/or enumeration of enterobacteria in a sample. The person skilled in the art will be, in this respect, fully capable of selecting these additional constituents. By way of example, the latter may be magnesium sulfate at a concentration of between 5 mM and 100 mM, preferably 20 mM, and/or at least one antibiotic.

Another object of the invention is the use of at least one chromogenic and/or fluorogenic phosphatase substrate for the detection and/or enumeration of enterobacteria in a sample likely to contain them, such as a food sample, and simultaneously or sequentially, at least one chromogenic and/or fluorogenic β-glucuronidase substrate to identify, among the enterobacteria detected via said phosphatase substrate, the β-glucuronidase-positive enterobacteria, for example the β-glucuronidase-positive *E. coli*.

Indeed, besides the presence and number of enterobacteria colonies, another essential factor to take into consideration in the quality control of human and veterinary foods is the number of β-glucuronidase-positive enterobacteria. Indeed, these β-glucuronidase-positive enterobacteria are known to possess a high pathogenic capacity. This is particularly true for β-glucuronidase-positive *Escherichia coli*. Furthermore, their detection is governed by standard ISO 16649-2, entitled "Microbiology of food and animal feeding stuffs—Horizontal method for the enumeration of beta-glucuronidase-positive *Escherichia coli*".

This particularly preferred embodiment of the invention therefore satisfies a two-fold requirement: detecting and/or enumerating the total enterobacteria in a sample on the one hand, and identifying and/or enumerating, among these total enterobacteria, the potentially pathogenic, or even highly pathogenic, β-glucuronidase-positive enterobacteria, on the other hand.

As stated above, the enterobacteria colonies are detected by the appearance of reactions of a first colour and/or fluorescence produced by the phosphatase activity of the enterobacteria on the phosphatase substrate. β-glucuronidase-positive enterobacteria (for example β-glucuronidase-positive *E. coli*) exhibit a "third coloration and/or fluorescence" (composite colour and/or fluorescence) due to the mixture of colours and/or fluorescences between the first colour and/or fluorescence and the second colour and/or fluorescence produced by the β-glucuronidase activity of the β-glucuronidase-positive enterobacteria.

This makes it possible to view (with the naked eye or via an electronic device such as a videocamera or photographic apparatus), in a cultured sample, both the enterobacteria in general, but also the β-glucuronidase-positive enterobacteria (in particular the β-glucuronidase-positive *E. coli*), with greater specificity than for the media used in the prior art (such as the REBECCA® medium). Specificity is understood to mean the ability to give a negative result when the target bacterial strain is not present. In other words, according to the present invention, more specific identification corresponds to reducing the number of false positives due to strains not expressing the enzymatic activities sought, without claiming to inhibit all of these strains.

Use of at least one phosphatase substrate and at least one β-glucuronidase substrate makes it possible to detect and/or enumerate enterobacteria (exhibiting a first colour and/or fluorescence) and, among the latter, β-glucuronidase-positive enterobacteria (exhibiting a third coloration and/or fluorescence, a mixture of said first coloration and/or fluorescence and a second coloration and/or fluorescence) from a sample (for example a food sample). Moreover, the detection and/or enumeration of phosphatase activity and beta-glucuronidase activity may be performed simultaneously in the same medium, without inhibition of one by the substrate of the other, that is to say without inhibition of the beta-glucuronidase activity by the phosphatase substrate, nor of the phosphatase activity by the beta-glucuronidase substrate.

Furthermore, neither the phosphatase substrate nor the β-glucuronidase substrate inhibit bacteria growth during the sample culturing step (for example taken from a given food sample). This makes it possible to perform reliable and robust microbiological tests.

The definition of the phosphatase substrate, within the terms of the present invention, applies mutatis mutandis to that of the beta-glucuronidase substrate with regard to the choice of its marker part. Thus "chromogenic and/or fluorogenic β-glucuronidase substrate" should be understood to mean an enzyme substrate capable, after reaction with a β-glucuronidase enzyme, of giving rise to a coloured and/or fluorescent reaction. The possible enzyme-substrate reactions are well known to the person skilled in the art. They may be cleavage reactions (for example by hydrolysis of the enzyme substrate), reduction, etc.

The chromogenic and/or fluorogenic β-glucuronidase substrates used according to the present invention are, preferably, synthetic substrates, comprising two parts (preferably consisting of two parts), a first part specific to the enzymatic activity to be detected, namely β-glucuronidase enzymatic activity, and a second part acting as a marker, hereafter referred to as the chromogenic and/or fluorogenic marker part. Said marker part is deemed "chromogenic and/or fluorogenic" insofar as, when it is no longer associated with the first part, namely after cleavage by the enzyme β-glucuronidase (for example as part of a hydrolysis reaction) and separation of said first and second parts, said marker part produces a coloration and/or a fluorescence. In other words, said chromogenic and/or fluorogenic marker part is capable, under certain conditions, of giving rise to a coloured and/or fluorescent reaction.

According to the present invention, the marker part of the chromogenic and/or fluorogenic β-glucuronidase substrate is preferably chosen from substrates based on indoxyl (3-Indoxyl, 5-Bromo-3-indoxyl, 5-Iodo-3-indoxyl, 4-Chloro-3-indoxyl, 5-Bromo-4-chloro-3-indoxyl, 5-Bromo-6-chloro-3-indoxyl, 6-Bromo-3-indoxyl, 6-Chloro-3-indoxyl, 6-Fluoro-3 indoxyl, 5-Bromo-4-chloro-N-methyl-3-indoxyl, N-Methyl-3-indoxyl, Aldo® . . . ); on umbelliferone (4-Methylumbelliferone, Cyclohexenoesculetin, . . . ); on alizarin; on p-naphtholbenzein; on Nitrophenol (ortho-Nitrophenol, para-Nitrophenol, . . . ); on Hydroxyquinoline; on Catechol (Catechol, Dihydroxyflavone, Hydroxy-flavone, . . . ); on Resorufin; on Chlorophenol Red; on Fluorescein; on Aminophenol (para-Aminophenol, Dichloro-aminophenol, . . . ); on Naphthol (alpha-Naphthol, 2-Naphthol, Naphthol-ASBI, . . . ); on Aminocoumarin (7-Amino-4-methyl-coumarin, . . . ); on Naphthylamide; on Acridine (Amino-phenyl-acridine . . . ); on Amino-phenoxazine (Amino-benzophenoxazinone, Amino-pentyl-resorufin, . . . ).

Preferably, the chromogenic and/or fluorogenic β-glucuronidase enzyme substrates used according to the present invention are selected from:

4 methylumbelliferyl-beta-glucuronide, substrates based on indoxyl or a derivative thereof, such as 5 bromo-4 chloro-3 indoxyl-beta-glucuronide, 5 bromo-6 chloro-3 indoxyl-beta-glucuronide, 6 chloro-3 indoxyl-beta-glucuronide), preferably 6-chloro-3-indoxyl-β-glucuronide, alizarin-beta-glucuronide and cyclohexenoesculetin-beta-glucuronide or salts thereof, preferably said at least one beta-glucuronidase substrate being at least one substrate based on indoxyl or a derivative thereof.

Advantageously the beta-glucuronidase substrate is 6-chloro-3-indoxyl-β-glucuronide ("Rose β-Glucuronide").

Just like the phosphatase substrate, the beta-glucuronidase substrate is preferably a chromogenic substrate, advantageously cleavable by the β-glucuronidase activity of the enterobacteria. Thus this β-glucuronidase substrate is preferably a substrate consisting of a target part and a marker part. Hydrolysis of the substrate by the β-glucuronidase activity of the β-glucuronidase-positive enterobacteria causes the separation (cleavage) of the target part and the marker part, said target part characterizing the β-glucuronidase enzymatic activity and said marker part being a molecule which makes it possible to reveal the hydrolysis reaction via a coloured reaction.

Just like 5-bromo-3-indoxyl phosphate ("Blue-Phosphate"), 6-chloro-3-indoxyl-beta-glucuronide ("Rose-beta-Glucuronide") makes it possible to achieve a highly satisfactory detection sensitivity, and consequently, easily detect beta-glucuronidase-positive enterobacteria.

When the preferred pair of enzyme substrates 5-bromo-3-indoxyl phosphate and 6-chloro-3-indoxyl-beta-glucuronide are used, the enterobacteria other than β-glucuronidase-positive are coloured blue (cleavage of "Blue-Phosphate"), the majority of the Gram- non-enterobacteria (for example non-fermenting Gram-) are not coloured (no phosphatase and β-glucuronidase activity), and β-glucuronidase-positive enterobacteria (for example β-glucuronidase-positive *E. coli*) appear "purplish" (colour varying from dark pink to violet). The purplish coloration is due to the mixture of blue and pink colours (cleavage of both "Blue-Phosphate" and "Rose-beta-Glucuronide" by the β-glucuronidase-positive enterobacteria possessing both enzymatic activities).

According to a particularly preferred embodiment, the phosphatase substrate and/or β-glucuronidase substrate is/are one or more substrate(s) based on indoxyl or a derivative thereof used in combination with an agent promoting oxidative polymerization of the indoxyl derivative such as an ammonium ferric citrate metal complex.

As an indoxyl-based β-glucuronidase substrate, mention may be made of 5 Bromo-4 chloro-3 indoxyl-beta-glucuronide, 5 Bromo-6 chloro-3 indoxyl-beta-glucuronide, 6 Chloro-3 indoxyl-beta-glucuronide ("Rose β-Glucuronide"), the latter compound being the preferred beta-glucuronidase substrate, as indicated above.

The agent promoting oxidative polymerization of the indoxyl derivative is as defined above, and is used at the above-mentioned concentrations.

The concentration at which the chromogenic and/or fluorogenic β-glucuronidase substrate must be used in the culture medium containing the sample is easily determinable by the person skilled in the art based on their general knowledge, and if applicable, routine tests. This concentration must be sufficient to achieve the requisite detection sensitivity level, but must not be excessive, so as not to risk inhibiting the enterobacteria growth. By way of example, the concentration of this β-glucuronidase substrate in the culture medium containing the sample to be tested is between approximately 0.1 and approximately 0.3 g/L, preferably between approximately 0.15 and 0.25 g/L, advantageously of around 0.175 g/L.

Preferably, said phosphatase substrate and said β-glucuronidase substrate are contained in a composition comprising at least one, preferably two, and advantageously three of the following constituents:

a bacterial culture medium suited to the bacteria to be detected (enterobacteria), an anti-Gram-positive selective system, an antifungal agent.

Each of the three above-mentioned constituents is as defined above.

Advantageously, said composition comprises a bacterial culture medium suited to the bacteria to be detected (enterobacteria) and at least one of, and preferably both of, the following two constituents:

an anti-Gram-positive selective system, an antifungal agent.

Another object of the present invention relates to the composition per se, as defined above, namely comprising at least one chromogenic and/or fluorogenic phosphatase substrate and at least one chromogenic and/or fluorogenic β-glucuronidase substrate. According to a particularly preferred embodiment, this composition is a chromogenic and/or fluorogenic reaction medium, consisting of both a culture medium and a revealing medium.

As explained in the course of the present application, this composition makes it possible to detect the presence of enterobacteria in a sample via their phosphatase activity and the β-glucuronidase substrate makes it possible to identify, among said enterobacteria thus detected, the β-glucuronidase-positive enterobacteria via their β-glucuronidase activity, for example β-glucuronidase-positive *E. coli*.

Advantageously, the phosphatase substrate and/or β-glucuronidase substrate is/are one or more substrate(s) based on indoxyl or a derivative thereof, said composition comprising an agent promoting oxidative polymerization of the indoxyl derivative of said phosphatase substrate and/or said β-glucuronidase substrate, such as an ammonium ferric citrate metal complex.

Another object of the present invention concerns the use of said composition to detect the presence of enterobacteria in a sample via their phosphatase activity and identify, among the enterobacteria thus detected, the β-glucuronidase-positive enterobacteria via their β-glucuronidase activity, for example β-glucuronidase-positive *E. coli*.

The present invention also concerns a method of detection and/or enumeration of enterobacteria in a sample likely to contain said enterobacteria, such as a food sample, said method comprising the following steps:

a) bring said sample into the presence of at least one chromogenic and/or fluorogenic phosphatase substrate, b) incubate at a sufficient temperature and for a sufficient period of time to allow the growth of the enterobacteria likely to be present in the sample, c) detect and/or enumerate the enterobacteria colonies via the appearance of coloured and/or fluorogenic reactions, said coloured and/or fluorogenic reactions being produced by the phosphatase activity of the enterobacteria on said at least one phosphatase substrate.

The phosphatase substrate(s) used is/are as defined above.

The person skilled in the art, based on their general knowledge and, if necessary, routine tests, will easily be able to determine the optimum temperature and time parameters for the incubation phase b). Preferably, this incubation phase consists in bringing the sample (and possibly an appropriate culture medium) to, and keeping it at, an appropriate temperature (determinable by the person skilled in the art), generally between 20 and 50° C., preferably between 30 and 40° C., for between 1 and 48 hours, preferably between 4 and 24 hours, more preferably between 16 and 24 hours.

According to a preferred embodiment, step a) is performed by placing said sample into contact with a composition comprising said phosphatase substrate and at least one bacterial culture medium.

Preferably, said composition comprises at least one anti-Gram-positive selective system and/or at least one antifungal, for example said composition containing at least one anti-Gram-positive selective system and at least one antifungal.

According to a particularly preferred embodiment, at step a), the sample is brought into the presence of a composition comprising at least one chromogenic and/or fluorogenic phosphatase substrate and at least one chromogenic and/or fluorogenic β-glucuronidase substrate, and wherein step c) is used to detect the appearance of reaction(s) of a first colour and/or fluorescence produced by the phosphatase activity of the enterobacteria on said phosphatase substrate and, simultaneously or sequentially (preferably simultaneously), the appearance of reactions of a second colour and/or fluorescence produced by the β-glucuronidase activity of the β-glucuronidase-positive enterobacteria, for example β-glucuronidase-positive E. coli. The incubation step b), meanwhile, is performed at a temperature and for a period known to—or easily determinable by—the person skilled in the art, appropriate for allowing a reaction detectable in step c), The β-glucuronidase substrate(s) used is/are as defined above.

Preferably, step a) of the method according to the invention is performed by culturing said sample with a composition comprising said phosphatase substrate, said β-glucuronidase substrate and at least one bacterial culture medium.

Another object of the invention is a method of detection and/or enumeration of enterobacteria in a sample likely to contain them, said method comprising the following steps:
a) Take said sample,
b) Bring the sample taken in step a) into contact with a composition comprising at least one chromogenic and/or fluorogenic phosphatase substrate and at least one chromogenic and/or fluorogenic β-glucuronidase substrate,
c) Possibly incubate the assembly at a temperature and for a period of time suitable to allow the growth of said enterobacteria,
d) Detect and/or enumerate:
the enterobacteria, preferably their colony (colonies), exhibiting a first coloration and/or fluorescence produced by the phosphatase activity of said enterobacteria on said phosphatase substrate, and simultaneously or sequentially, preferably simultaneously,
the β-glucuronidase-positive enterobacteria, for example β-glucuronidase-positive E. coli, preferably their colony (colonies), exhibiting a composite coloration and/or fluorescence produced by the mixture of said first coloration and/or fluorescence and a second coloration and/or fluorescence produced by the β-glucuronidase activity of said β-glucuronidase-positive enterobacteria.

Advantageously this detection and/or enumeration method includes the incubation step c).

DETAILED DESCRIPTION OF THE INVENTION

EXAMPLE 1

Specificity of Phosphatase Substrates for Enterobacteria 1.1. Media and Micro-Organisms 38 bacterial strains, among which 31 enterobacteria and 7 non-enterobacteria, were tested on media containing various phosphatase substrates. Readings of the dishes were then taken at 24 h.

The composition of the media is presented in Table 1 below:

TABLE 1

| Base common to all media (chromID ® Coli medium base ref. 42017 - mentioned in the foreword: | |
|---|---|
| Compounds | Conc. in g/L |
| Porcine gelatin peptone | 5.5 |
| Yeast extract | 8 |
| European agar | 12.5 |
| Sodium chloride | 5 |
| Sodium deoxycholate | 0.7 |
| Crystal violet | 0.001 |
| Niaproof 4 | 0.55 ml/l |

Then phosphatase substrates are added as follows:
Medium 1: addition of X-phosphate (X-P) at 60 mg/l
Medium 2: addition of Rose-phosphate (Rose-P) at 300 mg/L
Medium 3: addition of Magenta-phosphate (Magenta-P) at 300 mg/L
Medium 4: addition of Purple-phosphate (Purple-P) at 200 mg/L 1.2. Test The media are divided into Petri dishes.

Inoculation is performed from 24 h pre-cultures at 30° C. or 37° C., depending on the species, on Trypticase-soy medium.

Suspension in 0.5 McF physiological water is performed, and then the strains are inoculated with a 10 µl calibrated oese.

Readings are taken after 24 h and 48 h of incubation at 37° C.

1.3. Results

Thus, after 24 and 48 h of incubation, the following are obtained:
Green coloration of the colonies on medium 1,
Pink coloration of the colonies on medium 2,
Violet coloration of the colonies on media 3 and 4.

Colonies with coloration intensities greater than or equal to 1 were considered positive, applying the reading scale below.

Reading scale of enzymatic activity/coloration
0=no activity
0.5=very pale coloration
1=low-intensity distinct coloration
2=medium-intensity obvious coloration
3=intense coloration present,
4=highly intense coloration present.

The results are presented in Table 2 below:

TABLE 2

|  |  |  | X-P | Rose-P | Magenta-P | Purple-P |
|---|---|---|---|---|---|---|
| Entero-bacteria | 24 h | growth | 30/31 | 30/31 | 30/31 | 26/31 |
|  |  | coloration >= 1 | 90% | 77% | 90% | 83% |
|  | 48 h | growth | 31/31 | 31/31 | 31/31 | 31/31 |
|  |  | coloration | 97% | 94% | 100% | 100% |
| % positive non-fermenting Gram-negative | 24 h | growth | 7/7 | 5/7 | 5/7 | 5/7 |
|  |  | coloration >= 1 | 0% | 0% | 0% | 0% |
|  | 48 h | growth | 7/7 | 7/7 | 7/7 | 7/7 |
|  |  | coloration >= 1 | 0% | 0% | 0% | 0% |

1.4. Interpretation

Depending on the substrate used, coloration for at least 77% of the enterobacteria strains is obtained at 24 h, and at 48 h coloration for at least 94% of them is obtained. The X-phosphate and Magenta-phosphate substrates seem to be the most sensitive at 24 h. At 48 h, the results obtained are largely identical for X-phosphate, Magenta-phosphate and Purple-phosphate. Rose-phosphate is the least sensitive substrate at 24 h and 48 h.

Of the 7 non-fermenting Gram-negative strains, none provided a coloration greater than or equal to 1, regardless of the substrate used.

1.5. Conclusion

The very good sensitivity and very good specificity of the phosphatase substrates with regard to enterobacteria make them, surprisingly, prime markers for the detection and/or enumeration of the latter.

EXAMPLE 2

E. coli Enterobacteria Discrimination

2.1. Media and Micro-Organisms 13 bacterial strains, of which 3 *E. coli* and 10 enterobacteria not belonging to the species *E. coli*, were tested on media containing a combination of phosphatase and beta-glucuronidase substrates. Readings of the dishes are then taken at 24 h and 48 h. The composition of the media is presented in Table 3 below:

TABLE 3

| Base common to all media: | |
|---|---|
| Compounds | Conc. in g/l |
| Porcine gelatin peptone | 5.5 |
| Yeast extract | 8 |
| European yeast | 12.5 |
| Sodium chloride | 5 |
| Glucuronate | 0.2 |

TABLE 3-continued

| Base common to all media: | |
|---|---|
| Compounds | Conc. in g/l |
| Sodium deoxycholate | 0.7 |
| Ammonium ferric citrate | 0.3 |
| Crystal violet | 0.001 |
| Niaproof 4 | 0.55 ml/l |

Then the following substrate combinations are added (as an additive):
- Medium 1: 100 mg/L of X-β-GUR and 300 mg/L of Rose-phosphate (Rose-P),
- Medium 2: 100 mg/L of X-β-GUR and 200 mg/L of Magenta-phosphate (Magenta-P),
- Medium 3: 200 mg/L of Rose-β-GUR and 100 mg/L of X-phosphate (X-P),
- Medium 4: 200 mg/L of Rose-β-GUR and 200 mg/L of Blue-phosphate (Blue-P),
- Medium 5: 300 mg/L of magenta-β-GUR and 100 mg/L of X-phosphate (X-P),
- Medium 6: 300 mg/L of magenta-β-GUR and 200 mg/L of Blue-phosphate (Blue-P).

2.2. Tests

The media are maintained at 55° C. in order to perform pour plate inoculation. To do so, 0.5 McF bacterial suspensions are prepared from 24 h pre-cultures on trypticase-soy agar, incubated at 30 or 37° C. depending on the strains. These suspensions are then diluted to $1/250000^{th}$ and 300 μl are deposited in the bottom of dishes 90 mm in diameter and then covered with 18 ml of medium.

Readings are taken after 24 h at 37° C.

2.3. Results

The results obtained on the various media, after 24 h of incubation at 37° C., are presented in Table 4 below:

TABLE 4

|  |  | Medium 1 X-β-GUR + Rose-P | Medium 2 X-β-GUR + Magenta-P | Medium 3 Rose-β-GUR + X-P | Medium 4 Rose-β-GUR + Blue-P | Medium 5 magenta-β-GUR + X-P | Medium 6 magenta-β-GUR + Blue-P |
|---|---|---|---|---|---|---|---|
| E. coli | Coloration | Violet | Green | Pink | Pink | Violet | Violet |
|  | % coloured | 100 | 100 | 100 | 100 | 100 | 100 |
| Enterobacteria (non-E. coli) | Coloration | Pink | Violet | Green | Blue | Green | Blue |
|  | % coloured | 100 | 100 | 90 | 90 | 90 | 90 |

2.4. Interpretation

All the media make possible a good distinction between *E. coli* and enterobacteria. On media 3 to 6, only one strain of *Shigella* spp gives a coloration close to that expected for *E. coli*, this strain possessing beta-glucuronidase activity. From a genomic point of view, the *Shigella* strains belong to the species *E. coli*. What is more, "locking down" a food batch containing shigellae because of a suspicion of the presence of *E. coli* is not overly problematic, since shigellae have a recognised pathogenic capacity.

2.5. Conclusion

The combination of phosphatase and β-glucuronidase substrates does allow β-glucuronidase-positive *E. coli* to be distinguished from enterobacteria on the same medium. Indeed, the enterobacteria colonies exhibit a colour corresponding to the marker part of the phosphatase substrate used (pink for Rose-P, violet for Magenta-P, etc.). Conversely, the *E. coli* colonies exhibit a third coloration, resulting from the mixture between the colour produced by the marker part of the β-glucuronidase substrate and that produced by the marker part of the phosphatase substrate.

EXAMPLE 3

Evaluation of a Pair of Chromogenic Substrates on a Wide Panel of Bacterial Strains and Comparison with the REBECCA® Medium by AES (Mentioned in the Preamble of the Present Application)

3.1. Medium and Micro-Organisms 86 strains (see appendices 1 and 2), of which 5 *E. coli*, 48 enterobacteria, 23 Gram negative non-enterobacteria, 8 Gram positive and 2 yeasts, were tested on a prototype medium (comprising Rose-β-GUR and Blue-phosphate) and on the REBECCA® medium by AES (medium for the detection and/or enumeration of β-glucuronidase-positive *E. coli* and enterobacteria).

The readings of the dishes are then taken at 24 h.

The REBECCA® medium is a bottled medium, it must be regenerated and doped with a supplement before use.

The prototype medium is presented in Table 5 below:

TABLE 5

| Compounds | Conc. in g/l |
| --- | --- |
| Porcine gelatin peptone | 5.5 |
| Yeast extract | 7 |
| European agar | 12.5 |
| Sodium chloride | 5 |
| Ammonium ferric citrate | 0.3 |
| Glucuronate | 0.2 |
| Glucose | 0.1 |
| TRIS | 0.4 |
| Rose-β-GUR | 0.175 |
| Blue-Phosphate | 0.175 |
| Sodium deoxycholate | 0.6 |
| Crystal violet | 0.001 |
| Niaproof 4 | 0.3 ml/l |

3.2. Tests

The media are maintained at 55° C. in order to perform pour plate inoculation. To do so, 0.5 McF bacterial suspensions are prepared from 24 h pre-cultures on TSA incubated at 30 or 37° C., depending on the strains. These suspensions are then diluted to $1/250000^{th}$ and 300 µl are deposited in the bottom of dishes 90 mm in diameter, and then covered with 18 ml of medium.

Readings are taken after 24 h at 37° C.

3.3. Results

The results are presented in Table 6 below:

TABLE 6

| | | REBECCA® | Prototype medium according to the invention |
| --- | --- | --- | --- |
| *E. coli* | growth | 5/5 | 5/5 |
| | *E. coli* specific coloration | 5/5 (green) | 5/5 (pink) |
| Eb | growth | 48/48 | 48/48 |
| | Eb specific coloration | 45/48 (red) | 46/48 (blue) |
| | Ec false positives* | 2/48 (green) | 2/48 (pink/violet) |
| | no coloration | 1/48 | 0/48 |
| Gram-negative non-Eb | growth | 11/22 | 10/22 |
| | coloration | 11/11 (red) | 5/10 (blue) |
| Gram-positive | growth | 2/9 | 3/9 |
| | coloration | 2/2 (red) | 0/3 |

TABLE 6-continued

| | | REBECCA® | Prototype medium according to the invention |
| --- | --- | --- | --- |
| Yeasts | growth | 0/2 | 0/2 |
| | coloration | — | — |

Key:
Eb = enterobacteria;
Ec = *E. coli*
*= the two strains giving a coloration close to that expected for *E. coli* are *Shigella* spp strains with β-glucuronidase activity.

3.4. Interpretation

On both media, good fertility is observed for the *E. coli* and enterobacteria strains, as well as equivalent selectivity (approximately ⅔ of non-*E. coli* strains and non-enterobacteria strains are inhibited in both cases).

Conversely, better specificity for enterobacteria is observed on the prototype medium according to the invention than on the REBECCA® medium. Indeed, of the 13 strains other than *E. coli* or enterobacteria which grew on the REBECCA® medium, 100% exhibit red coloration whereas only 38% are coloured blue on the prototype medium.

3.5. Conclusion

The combined use of Blue-phosphate and Rose-β-glucuronide substrates makes it possible to obtain very good specificity for the detection and discrimination of β-glucuronidase-positive *E. coli* and enterobacteria. This specificity, against all expectations, is greater than that observed on the REBECCA® medium by AES (only medium on the market to date for an application of this type).

The present invention can be employed in a liquid medium, in particular for water analysis. For the purposes of an analysis of this type, the following enzyme substrates can be employed:

at least one nitrophenyl-phosphate substrate (phosphatase substrate) and at least one 4-methyl-umbelliferyl-beta-D-glucuronide substrate (beta glucuronidase substrate);

at least one p-aminophenyl-phosphate substrate (phosphatase substrate) and at least one alpha-naphthol-beta-glucuronide substrate (beta glucuronidase substrate);

at least one X-phosphate substrate (phosphatase substrate) and at least one p-nitrophenyl-beta-glucuronide substrate (beta glucuronidase substrate).

APPENDIX 1

List of *E. coli* and Enterobacteria strains used in Example 3

| | species | source |
| --- | --- | --- |
| 1 | *E. coli* | ATCC 25922 |
| 2 | *E. coli* | CIP 54117 |
| 3 | *E. coli* | Turkey escalope |
| 4 | *E. coli* | Roquefort |
| 5 | *E. coli* | St Felicien |
| 1 | *Buttiauxella agrestis* | cooking sausage |
| 2 | *Citrobacter braakii* | fresh cream |
| 3 | *Citrobacter freundii* | piedmont salad |
| 4 | *Citrobacter freundii* | cooking sausage |
| 5 | *Citrobacter koseri* | ATCC 27156 |
| 6 | *Edwardsiella tarda* | CIP 7861 |
| 7 | *Enterobacter amnigenus* | watercress |
| 8 | *Enterobacter cloacae* | ravioli de romans |
| 9 | *Enterobacter cloacae* | cooked prawns |
| 10 | *Enterobacter intermedius* | chicken drumsticks |
| 11 | *Enterobacter sakazakii* | rodent food |
| 12 | *Enterobacter sakazakii* | agri-food |
| 13 | *Escherichia hermannii* | Veterinary |

APPENDIX 1-continued

List of *E. coli* and Enterobacteria strains used in Example 3

| | species | source |
|---|---|---|
| 14 | *Ewingella americana* | chicken fillet |
| 15 | *Ewingella americana* | sausage meat |
| 16 | *Hafnia alvei* | calf's foot |
| 17 | *Hafnia alvei* | rocket |
| 18 | *Klebsiella oxytoca* | calf's foot |
| 19 | *Klebsiella pneumoniae* ssp *pneumoniae* | CIP 8291 |
| 20 | *Kluyvera ascorbata* | CIP 8295 |
| 21 | *Kluyvera intermedia* | |
| 22 | *Leclercia adecarboxylata* | environment |
| 23 | *Morganella morganii* ssp *morganii* | environment |
| 24 | *Pantoea agglomerans* | lamb's lettuce |
| 25 | *Pantoea agglomerans* | lettuce |
| 26 | *Pectobacterium carotovorum* | |
| 27 | *Pectobacterium carotovorum* | |
| 28 | *Proteus mirabilis* | Fac pharma |
| 29 | *Proteus mirabilis* | chicken |
| 30 | *Proteus vulgaris* | QI-82 LeMoulis |
| 31 | *Proteus vulgaris* | Goat ravioli |
| 32 | *Providencia stuartii* | Veterinary |
| 33 | *Rahnella aquatilis* | Olive pate |
| 34 | *Rahnella aquatilis* | Vegetable pate |
| 35 | *Raoultella ornithinolytica* | Turkey escalope |
| 36 | *Salmonella* ser. *Enteritidis* | CIP 8297 = ATCC 13076 |
| 37 | *Salmonella* ser. *Typhimurium* | CIP 5858 = ATCC 13311 |
| 38 | *Salmonella* spp | agri-food |
| 39 | *Salmonella* spp | agri-food |
| 40 | *Serratia liquefaciens* | lettuce |
| 41 | *Serratia liquefaciens* | chicken drumsticks |
| 42 | *Shigella boydii* | |
| 43 | *Shigella flexneri* | CIP 8248 = ATCC 29903 |
| 44 | *Shigella sonnei* | CIP 8249 = ATCC 29930 |
| 45 | *Yersinia enterocolitica* | calf's foot |
| 46 | *Yersinia enterocolitica* | pork brains |
| 47 | *Yersinia enterocolitica* spp *enterocolitica* | CIP 8027 |

APPENDIX 2

List of Gram negative, Gram positive and yeast strains used in Example 3

| | | Species | source |
|---|---|---|---|
| Gram− | 1 | *Acinetobacter baumanii* | QI 327 lamb's lettuce |
| | 2 | *Acinetobacter calcoacet* | |
| | 3 | *Acinetobacter lwoffi* | veal escalope |
| | 4 | *Aeromonas hydrophila/caviae* | QI 206 Poultry gizzard |
| | 5 | *Aeromonas hydrophila/caviae* | QI 216 Veal liver |
| | 6 | *Aeromonas sobria* | |
| | 7 | *Aeromonas sobria* | QI 179 Chicken drumsticks |
| | 8 | *Aeromonas sobria* | QI 259 Pork spare rib |
| | 9 | *Burkolderia cepacia* | QI 257 Pork spare rib |
| | 10 | *Chryseobacterium indologenes* | Dairy product |
| | 11 | *Moraxella lacunata* | Veterinary |
| | 12 | *Plesiomonas shigelloides* | Veterinary |
| | 13 | *Pseudomonas alcaligenes* | Industry |
| | 14 | *Pseudomonas fluorescens* | QI 300 Pork tenderloin |
| | 15 | *Pseudomonas lundensis* | QI 291 Veal escalope |
| | 16 | *Pseudomonas putida* | QI 268 Rocket |
| | 17 | *Pseudomonas stutzeri* | Cheese |
| | 18 | *Shewanelle putrefaciens* | Veterinary |
| | 19 | *Stenotrophomonas maltophilia* | |
| | 20 | *Vibrio harveyi* | Water |
| | 21 | *Vibrio parhaemolyticus* | Water |
| | 22 | *Vibrio* spp | QI 49 Sea water |
| Gram+ | 1 | *Aerococcus viridans* | QI 21 Fresh fish fillet |
| | 2 | *Bacillus cereus* | Custard |
| | 3 | *Bacillus circulans* | |
| | 4 | *Enterococcus faecalis* | |
| | 5 | *Enterococcus faecium* | QI 310 Emmental |
| | 6 | *Lactobacillus plantarum* | Veterinary |

APPENDIX 2-continued

List of Gram negative, Gram positive and yeast strains used in Example 3

| | | Species | source |
|---|---|---|---|
| | 7 | *Lactococcus lactis* ssp *lactis* | |
| | 8 | *Staphylococcus aureus* ssp *aureus* | |
| | 9 | *Staphylococcus epidermidis* | QI 124 Muesli |
| Yeasts | 1 | *Candida albicans* | Veterinary |
| | 2 | *Saccharomyces cerevisiae* | Cream |

The invention claimed is:

1. A method for specifically detecting, enumerating and/or identifying fermenting, Gram-negative enterobacteria in a sample comprising fermenting, Gram-negative enterobacteria and non-fermenting, Gram-negative bacteria, and discriminating the fermenting, Gram-negative enterobacteria from the non-fermenting, Gram-negative bacteria, the method comprising:

contacting the sample with a reaction medium comprising:
a) a chromogenic and/or fluorogenic phosphatase substrate capable of producing a first coloration and/or fluorescence in the presence of a phosphatase activity, and
b) a chromogenic and/or fluorogenic β-glucuronidase substrate capable of producing a second coloration and/or fluorescence in the presence of a β-glucuronidase activity, allowing the fermenting, Gram-negative enterobacteria to react with the chromogenic and/or fluorogenic phosphatase substrate and at least a portion of the fermenting, Gram-negative enterobacteria to react with the chromogenic and/or fluorogenic β-glucuronidase substrate to form colonies having the first coloration and/or fluorescence and colonies having a composite coloration and/or fluorescence produced by a mixture of the first coloration and/or fluorescence and the second coloration and/or fluorescence, observing the first coloration and/or fluorescence and specifically detecting, enumerating and/or identifying, in said reaction medium, phosphatase positive fermenting, Gram-negative enterobacteria having the first coloration and/or fluorescence, observing a composite coloration and/or fluorescence produced by a mixture of the first coloration and/or fluorescence and the second coloration and/or fluorescence and specifically detecting, enumerating and/or identifying, in said reaction medium, phosphatase and β-glucuronidase positive fermenting, Gram-negative enterobacteria having the composite coloration and/or fluorescence, and observing no first coloration and/or fluorescence, no second coloration and/or fluorescence and no composite coloration and/or fluorescence corresponding to the non-fermenting, Gram-negative bacteria colonies.

2. The method according to claim 1, wherein the chromogenic and/or fluorogenic β-glucuronidase substrate comprises a synthetic substrate having a first part specific to β-glucuronidase activity, and a second chromogenic and/or fluorogenic marker part.

3. The method according to claim 1, wherein β-glucuronidase substrate comprises 4 methylumbelliferyl-β-glucuronide, an indoxyl or a derivative thereof, alizarin-β-glucuronide, or cyclohexenoesculetin-β-glucuronidase or salts thereof.

4. The method according to claim 1, wherein one or more of the phosphatase substrate and the β-glucuronidase substrate comprises an indoxyl or a derivative thereof and wherein the step of contacting the sample with the reaction medium further comprises contacting the sample with an agent for promoting oxidative polymerisation of the indoxyl or derivative thereof.

5. The method according to claim 4, wherein the agent comprises an ammonium ferric citrate metal complex.

6. The method according to claim 1, wherein the reaction medium comprises one or more of the following constituents:
a bacterial culture medium suited to the bacteria to be detected,
one or more anti-Gram-positive selective agent(s), and
an antifungal agent.

7. The method according to claim 1, wherein the contacting comprises incubating the sample with the composition at a temperature and time period sufficient to grow the fermenting, Gram-negative enterobacteria.

8. The method according to claim 1, wherein the fermenting, Gram-negative enterobacteria comprises colonies.

9. The method according to claim 1, wherein the detection of the first coloration and/or fluorescence and the detection of the composite coloration and/or fluorescence are performed substantially simultaneously.

10. The method according to claim 1, wherein the sample comprises a food sample.

11. The method according to claim 1, wherein the phosphatase and β-glucuronidase -positive fermenting, Gram-negative enterobacteria are *E. Coli*.

12. The method according to claim 1, wherein the β-glucuronidase substrate comprises 6-chloro-3-indoxyl-β-glucuronide.

13. The method according to claim 1, wherein the β-glucuronidase substrate is selected from the group consisting of 5-bromo-4chloro-3-indoxyl-β-glucuronide, 5-bromo-6cloro-3-indoxyl-β-glucuronide, and 6-chloro-3-indoxyl-β-glucuronide.

14. The method of claim 1, wherein the chromogenic and/or fluorogenic phosphatase substrate comprises:
a synthetic substrate having a fist part specific to phosphatase activity, and
a second chromogenic and/or fluorogenic marker part.

15. The method of claim 1, wherein the chromogenic and/or fluorogenic phosphatase substrate is selected from the group consisting of 5-bromo-4-chloro-3-indoxyl -phosphatae, 5-bromo-6-chloro-3-indoxyl-phosphate, 6-chloro-3-indoxyl-phosphate, 5-iodo-3 -indeoxyl-phosphate, 6-bromo-3-indoxyl-phosphate, 5,6-dibromo-3-indoxyl-phosphate and 5-bromo-3-indoxyl-phosphate.

16. The method of claim 1, wherein the at least one phosphatase positive fermenting, Gram-negative enterobacteria having the first coloration and/or fluorescence is selected from the group consisting or *Buttiauxella, Edwardsiella, Ewingella, Hafnia, Kluyvera, Leclercia, Morganella, Pantoea, Pectobacterium, Proteus, Providencia, Rahnella, Raoultella, Salmonella, Serratia, Shigella*, and *Yersinia*.

17. The method of claim 16, further comprising specifically detecting, enumerating and/or identifying a second phosphatase positive fermenting, Gram-negative enterobacteria in the sample having a coloration and/or fluorescence produced by the phosphatase activity of the fermenting, Gram-negative enterobacteria, wherein the second phosphatase positive fermenting, Gram-negative enterobacteria comprises *Escherichia* or *Citrobacter*.

18. The method of claim 17, wherein the *Escherichia* is selected from the group consisting of *E. coli* and *E. hermannii*.

19. The method of claim 1, wherein at least one phosphatase positive fermenting, Gram-negative enterobacteria having the first coloration and/or fluorescence is selected from the group consisting of *Salmonella, Shigella*, and *Yersinia*.

20. The method of claim 1, wherein the non-fermenting, Gram-negative bacteria are selected from the genuses *Acinetobacter, Aeromonas, Burkolderia, Chryseobacterium, Moraxella, Plesiomonas, Pseudomonas, Shewanella, Stenotrophomonas* and *Vibrio*.

21. The method of claim 1, wherein the non-fermenting, Gram-negative bacteria are selected from *Acinetobacter baumanii, Acinetobacter calcoacet, Acinetobacter lwoffi, Aeromonas hydrophila, Aeromonas caviae, Aeromonas sobria, Burkolderia cepacia, Chryseobacterium indologenese, Moraxella lacunata, Plesiomonas shigelloides, Pseudomonas stutzeri, Shewanella putrefaciens, Stenotrophomonas maltophilia, Vibrio harveyi*, and *Vibrio parhaemolyticus*.

22. The method of claim 1, wherein the reaction medium consists essentially of the chromogenic and/or fluorogenic phosphatase substrate, the chromogenic and/or fluorogenic β-glucuronidase substrate, and, optionally, one or more of a bacterial culture medium suited to the bacterial to be detected, an anti-Gram-positive selective system and an antifungal.

* * * * *

UNITED STATES PATENT AND TRADEMARK OFFICE
CERTIFICATE OF CORRECTION

PATENT NO. : 10,808,275 B2
APPLICATION NO. : 14/782122
DATED : October 20, 2020
INVENTOR(S) : Marie Cellier et al.

Page 1 of 1

It is certified that error appears in the above-identified patent and that said Letters Patent is hereby corrected as shown below:

In the Claims

Column 24, Line 37; Change "Plesiomonas shigelloïdes, Pseudomonas stutzeri," to --Plesiomonas shigelloïdes, Pseudomonas alcaligenes, Pseudomonas fluorescens, Pseudomonas lundensis, Pseudomonas putida, Pseudomonas stutzeri,--

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*